(12) United States Patent
Gostout

(10) Patent No.: US 8,221,443 B2
(45) Date of Patent: Jul. 17, 2012

(54) SUBMUCOSAL ENDOSCOPY WITH MUCOSAL FLAP METHODS AND KITS

(75) Inventor: Christopher J. Gostout, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 983 days.

(21) Appl. No.: 11/985,413

(22) Filed: Nov. 15, 2007

(65) Prior Publication Data

US 2008/0125804 A1    May 29, 2008

Related U.S. Application Data

(60) Provisional application No. 60/859,059, filed on Nov. 15, 2006.

(51) Int. Cl.
*A61M 29/00* (2006.01)
(52) U.S. Cl. .......................... 606/192; 606/191
(58) Field of Classification Search .......... 606/190–196, 606/228; 604/96.01
See application file for complete search history.

(56) References Cited

U.S. PATENT DOCUMENTS

| | | | |
|---|---|---|---|
| 5,368,930 A | 11/1994 | Samples | |
| 5,542,948 A | 8/1996 | Weaver et al. | |
| 6,021,524 A | 2/2000 | Wu et al. | |
| 6,080,474 A | 6/2000 | Oakley et al. | |
| 6,126,058 A | 10/2000 | Adams et al. | |
| 6,158,437 A * | 12/2000 | Vagley | 128/898 |
| 6,210,416 B1 | 4/2001 | Chu et al. | |
| 6,264,086 B1 | 7/2001 | McGuckin, Jr. | |
| 6,632,227 B2 | 10/2003 | Adams | |
| 2002/0161114 A1 | 10/2002 | Gunatillake et al. | |
| 2003/0225460 A1 | 12/2003 | Gostout et al. | |
| 2005/0267531 A1 * | 12/2005 | Ruff et al. | 606/228 |
| 2007/0260178 A1 * | 11/2007 | Skerven et al. | 604/96.01 |
| 2010/0168508 A1 * | 7/2010 | Gertner | 600/37 |

FOREIGN PATENT DOCUMENTS

WO    WO 2006/122279 A2    11/2006

OTHER PUBLICATIONS

Davidson et al., "Intrathoracic neural tumours," *Thorax*, 1978;33:359-367.
Sumiyama et al., "Transesophageal mediastinoscopy by submucosal endoscopy with mucosal flap safety valve technique," *Gastrointest. Endosc.*, Apr. 2007;65(4):679-683.
Sumiyama et al., "Submucosal endoscopy with mucosal flap safety valve," *Gastrointest. Endosc.*, Apr. 2007;65(4):688-694 [Epub Feb. 26, 2007].
ASGE/SAGES "Working Group on Natural Orifice Translumenal Endoscopic Surgery," White Paper, Oct. 2005, *Gastrointest. Endosc.*, 2006;63(2):199-203.

(Continued)

*Primary Examiner* — Eduardo C Robert
*Assistant Examiner* — Christina Negrelli
(74) *Attorney, Agent, or Firm* — Mueting, Raasch & Gebhardt, P.A.

(57) ABSTRACT

Kits and methods for submucosal endoscopic access into body cavities such as the peritoneal cavity and the posterior mediastinum through a submucosal endoscopic procedure in which an opening is formed through the muscularis propria within a bleb. The procedure may result in a mucosal flap formed by separated mucosal tissue within the bleb and the mucosal flap may be advantageously used to assist in closure of the opening.

16 Claims, 3 Drawing Sheets

OTHER PUBLICATIONS

Bassotti et al., "Interstitial cells of Cajal, enteric nerves, and glial cells in colonic diverticular disease," *J. Clin. Pathol.*, 2005;58:973-977.

Bergström et al., "Transgastric anastomosis by using flexible endoscopy in a porcine model (with video)," *Gastrointest. Endosc.*, 2006;63(2):307-312.

Chui et al., "Peroral transgastric endoscopic ligation of fallopian tubes with long-term survival in a porcine model," *Gastrointest. Endosc.*, 2005;62(3):472.

Conio et al., "Endoscopic Circumferential Esophageal Mucosectomy in a Porcine Model: An Assessment of Technical Feasibility, Safety, and Outcome," *Endosc.*, Sep. 2001;33:791-794.

de la Mora et al., "Intramural Endoscopic Dissection Using Pressurized Gas: A Novel Approach to Large Area Mucosal Resection and Polypectomy?" *Gastrointest. Endosc.*, 2004;59(5):P91.

Gaur, "Laparoscopic Operative Retroperitoneoscopy: Use of a New Device," *J. Urol.*, Oct. 1992;148:1137-1139.

Gaur et al., "Laparoscopic Condom Dissection: New Technique of Retroperitoneoscopy," *J Endourol.*, 1994;8(2):149-151.

Iishi et al., "Endoscopic resection of large pedunculated colorectal polyps using a detachable snare," *Gastrointest. Endosc.*, 1996;44(5):594-597.

Iishi et al., "Endoscopic Resection of Large Sessile Colorectal Polyps Using a Submucosal Saline Injection Technique," *Hepato-Gastroent.*, 1997;44:698-702.

Ishiguro et al., "Correlation of lifting versus non-lifting and microscopic depth of invasion in early colorectal cancer," *Gastrointest Endosc.*, 1999;50(3):329-333.

Jagannath et al., "Peroral transgastric endoscopic ligation of fallopian tubes with long-term survival in a porcine model," *Gastrointest. Endosc.*, 2005;61(3):449-453.

Kajiyama et al., "Endoscopic resection of gastrointestinal submucosal lesions: a comparison between strip biopsy and aspiration lumpectomy," *Gastrointest. Endosc.*, 1996;44(4):404-410.

Kalloo et al., "Flexible transgastric peritoneoscopy: a novel approach to diagnostic and therapeutic interventions in the peritoneal cavity," *Gastrointest. Endosc.*, 2004;60(1):114-117.

Kantsevoy et al., "Endoscopic gastrojejunostomy with survival in a porcine model," *Gastrointest. Endosc.*, 2005;62(2):287-292.

Kantsevoy et al., "Transgastric endoscopic splenectomy: Is it possible?," *Surg. Endosc.*, 2006;20:522-525.

Ko et al., "Per-oral transgastric abdominal surgery," *Chin. J. Dig. Dis.*, 2006;7:67-70.

Kodama et al., "Treatment of superficial cancer of the esophagus: A summary of responses to a questionnaire on superficial cancer of the esophagus in Japan," *Surgery*, Apr. 1998;123(4):432-439.

Lima et al., "Transvesical Endoscopic Peritoneoscopy: a Novel 5 mm Port for Intra-Abdominal Scarless Surgery," *J Urol.*, Aug. 2006;176:802-805.

Ohkuwa et al., "New Endoscopic Treatment of Intramucosal Gastric Tumors Using an Insulated-Tip Diathermic Knife," *Endoscopy*, 2001;33(3):221-226.

Ono, "Endoscopic suture for perforation due to EMR," (in Japanese with English abstract), *Endoscopia Digestiva*, Feb. 2002;14(2):187-192.

Pardi et al., "Paraneopolastic Dysmotility: Loss of Interstitial Cells of Cajal," *Am. J. Gastroenterol.*, 2002;97(7):1828-1833.

Park et al., "Experimental studies of transgastric gallbladder surgery: cholecystectomy and cholecystogastric anastomosis (videos)," *Gastrointest. Endosc.*, 2005;61(4):601-606.

Piotrowska et al., "Alterations in Smooth Muscle Contractile and Cytoskeleton Proteins and Interstitial Cells of Cajal in Megasystis Microcolon Intestinal Hypoperistalsis Syndrome," *J. Pediatr. Surg.*, May 2003;38(5):749-755.

Rajan et al., "Endoscopic Full Thickness Biopsy of the Stomach: What Works?" Abstract T1467, *Gastrointest. Endosc.*, Apr. 2006;63(5):AB233.

Rattner et al., "ASGE/SAGES Working Group on Natural Orifice Translumenal Endoscopic Surgery—Oct. 2005," *Surg. Endosc.*, 2006;20:329-333.

Ribet et al., "Neurogenic Tumors of the Thorax," *Ann. Thorac. Surg.*, 1994;58:1091-1095.

Rösch et al., "Attempted Endoscopic En Bloc Resection of Mucosal and Submucosal Tumors Using Insulated-Tip Knives: A Pilot Series," *Endoscopy*, 2004;36:788-801.

Silverman et al., "Mediastinal Masses," *Surg. Clin. North Am.*, Aug. 1980;60(4):757-777.

Sumiyama et al., "Closure of Gastric Perforation with a Novel Tissue Anchoring Device," Abstract 721, *Gastrointest. Endosc.*, Apr. 2006;63(5):AB101.

Swanstrom et al., "Development of a New Access Device for Transgastric Surgery," *J. Gastrointest. Surg.*, 2005;9(8):1129-1137.

Takayama et al., "The Interstitial Cells of Cajal and a Gastroenteric Pacemaker System," *Arch. Histol. Cytol.*, 2002;65(1):1-26.

Tong et al., "Study on distribution of interstitial cells of Cajal in the sigmoid colon of patients with slow transit constipation," (in Chinese with English abstract), *Zhonghau Waike Zazhi—Chin. J. Surg.*, Jul. 2004;42(14):853-856.

Tong et al., "Decreased interstitial cells of Cajal in the sigmoid colon of patients with slow transit constipation," *Int. J. Colorectal Dis.*, 2004;19:467-473.

Wagh et al., "Endoscopic Transgastric Abdominal Exploration and Organ Resection: Initial Experience in a Porcine Model," *Clin. Gastroenterol. Hepatol.*, 2005;3:892-896.

Wagh et al., "Survival studies after endoscopic transgastric oophorectomy and tubectomy in a porcine model," *Gastrointest. Endosc.*, 2006;63(3):473-478.

Wallace, "Take NOTES (Natural Orifice Transluminal Endoscopic Surgery)," *Gastroenterology*, 2006;131:11-12.

Whooley et al., "Primary Tumors of the Mediastinum," *J. Surg. Oncol.*, 1999; 70:95-99.

Yamamoto et al., "A novel method of endoscopic mucosal resection using sodium hyaluronate," *Gastrointest. Endosc.*, 1999;50(2):251-256.

\* cited by examiner

SUBMUCOSAL ENDOSCOPY WITH MUCOSAL FLAP METHODS AND KITS

RELATED APPLICATIONS

The present application claims the benefit of U.S. Provisional Application No. 60/859,059, titled SUBMUCOSAL ENDOSCOPY WITH MUCOSAL FLAP METHODS AND KITS, filed on Nov. 15, 2006, which is hereby incorporated by reference in its entirety.

The present invention relates to internal surgical devices and methods for performing submucosal endoscopies in which a mucosal flap can be used to seal an opening. More particularly, the present invention relates to devices that may beneficially be used in conjunction with, e.g., mucosectomy procedures, myotomies, etc.

A variety of approaches to access internal body cavities are used. In particular, access to the peritoneal cavity may be used to perform a variety of procedures.

Similarly, access to the posterior mediastinum may be required for a variety of procedures. For example, the posterior mediastinum contains important organs such as the descending thoracic aorta, esophagus, azygos vein, and autonomic ganglia and nerves. In addition, prevalent gastrointestinal surgeries such as transhiatal esophagectomy and vagotomy are performed in the posterior mediastinum. The posterior mediastinum is, however, remote from the body surface and bounded by critical and delicate organs, e.g., the pericardium, the posterior surface of the diaphragm, the vertebral column (from the lower border of the fourth to the twelfth thoracic vertebra, and by the mediastinal pleura.

Although percutaneous mediastinoscopy can be used to provide minimally invasive access to the mediastinal cavity, it still requires thoracotomy and pleural incision to provide access to the posterior mediastinum.

SUMMARY OF THE INVENTION

The present invention provides kits and methods for submucosal endoscopic access into body cavities such as the peritoneal cavity and the posterior mediastinum through a submucosal endoscopic procedure in which an opening is formed through the muscularis propria within a bleb. The procedure results in a mucosal flap formed by separated mucosal tissue within the bleb and the mucosal flap may be advantageously used to assist in closure of the opening.

Among the potential advantages of the kits and methods of the present invention may be, e.g., reducing or eliminating trauma to important surrounding organs by using the esophagus (one of the intramediastinal organs), stomach, etc. as the entry site into the posterior mediastinum, peritoneal cavity, etc.

Another potential advantage of using the submucosal bleb formation is the opportunity to perform a myotomy through the muscularis propria underlying the detached mucosal layer within a bleb formed by separating a mucosal tissue from the underlying muscularis propria. After the myotomy is performed, transesophageal access into the posterior mediastinum or trans-gastric access into the peritoneal cavity may be provided. When the access is no longer required (e.g., when the procedure in the posterior mediastinum or peritoneal cavity is completed), the mucosal flap formed by the overlying detached mucosal layer can be secured to close the access point.

The apparatus and methods for creating blebs may preferably involve the delivery of gas submucosally to separate tissue and create a gas-filled submucosal space. The gas may preferably be delivered at a pressure greater than atmospheric pressure. Using pressurized gas to create gas-filled blebs may provide a number of advantages over blebs formed using liquids. It has been observed that blebs created with pressurized gas may be higher, i.e., the gas-filled submucosal space may potentially be higher when measure normal to the plane of the underlying tissue. It has also been observed that tissue separation within the space of a gas-filled bleb may potentially be more pronounced than within a liquid-filled bleb.

Among the gases that may be used to form gas-filled blebs, it may be preferred that the gas used be carbon dioxide. Potential advantages of carbon dioxide may potentially include, e.g., that carbon dioxide is readily absorbed by tissue and is unlikely to cause embolisms. In addition, carbon dioxide is not flammable and is readily available. More particularly, it may be preferred that the gas used consist essentially of carbon dioxide. It should be understood that small amounts of liquid, such as water, saline, etc., may be entrained within the carbon dioxide so long as the fluid delivered to form a gas-filled bleb is predominantly in the gas phase.

In some embodiments of the invention, the elongated body may include a fluid delivery lumen extending to the distal end of the elongated body, with a needle attached to the fluid delivery lumen at the distal end of the elongated body. It may be preferred that the needle be movable between an injection position in which the needle extends from the distal end of the elongated body and a sheathed position in which the needle is located within the elongated body.

An apparatus of the present invention that includes a fluid delivery lumen and needle may further preferably include a fluid source connected to the fluid delivery lumen. The fluid source may provide a fluid as needed to form submucosal fluid cushions in accordance with the preset invention. The fluid provided by the fluid source may be a liquid as is conventionally known. Alternatively, the fluid sources of the present invention may provide a gas to form the submucosal fluid cushion in accordance with the present invention. The gas may be, e.g., carbon dioxide.

In one aspect, the present invention provides a kit for performing submucosal endoscopy with a mucosal flap, the kit including an endoscope having a proximal end and a distal end; a needle attached to a fluid delivery lumen capable of extending through at least a portion of the endoscope, wherein the needle is attached to a distal end of the fluid delivery lumen such that fluid passing through the distal end of the fluid delivery lumen passes through the needle; a fluid source adapted for connection to a proximal end of the fluid delivery lumen, the fluid source comprising a fluid adapted to form a bleb in which a mucosal tissue layer is separated from underlying muscularis propria; a resection apparatus capable of attaching to the distal end of the endoscope, wherein the resection apparatus is capable of forming an opening through the underlying muscularis propria within the bleb whereby one or more devices may be advanced through the opening; and tissue attachment materials capable of attaching the separated mucosal tissue layer to cover the opening formed in the underlying muscularis propria.

In various embodiments, the kits may further include the following features/additions: the resection apparatus may be an endoscopic mucosal resection cap attached to the distal end of the endoscope; the tissue attachment materials may include tissue anchors, tissue clips, tissue adhesive, suture material, etc.; the fluid in the fluid source may be a liquid; the fluid in fluid source may be a gas; the fluid in the fluid source may be held at a pressure of 20 psig (140 kPa) or more; etc. In some embodiments, the kit may include a mechanical expansion device (e.g., an inflatable balloon) adapted for delivery into the bleb between the separated mucosal tissue layer and the underlying muscularis propria through a lumen in the endoscope, wherein the mechanical expansion device has a collapsed configuration in which the mechanical expansion device passes through the lumen and an expanded configuration in which the mechanical expansion device expands to a size larger than the lumen.

In another aspect, the present invention may provide a method for accessing the mediastinum through the esophagus, the method involving use of a kit according to the present invention to form the opening through the muscularis propria of the esophagus into the mediastinum, whereby one or more devices may be advanced into the mediastinum through the opening; and using the kit to cover the opening by re-attaching at least a portion of the separated mucosal tissue layer to the muscularis propria.

In another aspect, the present invention may provide a method for accessing the peritoneal cavity through the stomach, the method involving the use of a kit according to the present invention to form the opening through the muscularis propria of the stomach into the peritoneal cavity, whereby one or more devices may be advanced into the peritoneal cavity through the opening; and using the kit to cover the opening by re-attaching at least a portion of the separated mucosal tissue layer to the muscularis propria.

In another aspect, the present invention may provide a method for accessing the mediastinum through the esophagus, the method including delivering a fluid into mucosal tissue at a selected site in the esophagus of a subject through a distal end of a fluid delivery lumen, wherein the fluid is delivered at a fluid pressure greater than the ambient atmospheric pressure, wherein the fluid separates the mucosal tissue to create a bleb in which a mucosal tissue layer is separated from underlying muscularis propria; advancing an endoscope into the bleb through the separated mucosal tissue layer; forming an opening through the muscularis propria of the esophagus within the bleb, whereby one or more devices may be advanced into the mediastinum through the opening; and covering the opening through the muscularis propria by re-attaching at least a portion of the separated mucosal tissue layer to the muscularis propria.

In another aspect, the present invention may provide a method for accessing the peritoneal cavity through the stomach, the method including delivering a fluid into mucosal tissue at a selected site in the stomach of a subject through a distal end of a fluid delivery lumen, wherein the fluid is delivered at a fluid pressure greater than the ambient atmospheric pressure, wherein the fluid separates the mucosal tissue to create a bleb in which a mucosal tissue layer is separated from underlying muscularis propria; advancing an endoscope into the bleb through the separated mucosal tissue layer; forming an opening through the muscularis propria of the stomach within the bleb, whereby one or more devices may be advanced into the peritoneal cavity through the opening; and covering the opening through the muscularis propria by re-attaching at least a portion of the separated mucosal tissue layer to the muscularis propria.

These and other potential features and advantages of the present invention may be described below in connection with various exemplary embodiments of the invention.

BRIEF DESCRIPTIONS OF THE FIGURES

DESCRIPTION OF EXEMPLARY
EMBODIMENTS OF THE INVENTION

In the following detailed description of some exemplary embodiments of the invention, reference is made to the accompanying figures which form a part hereof, and in which are shown, by way of illustration, specific embodiments in which the invention may be practiced. It is to be understood that other embodiments may be utilized and structural changes may be made without departing from the scope of the present invention.

The kits of the present invention may preferably include a number of components useful for performing submucosal endoscopy with a mucosal flap used to close an opening formed during the procedure. The kits may preferably include an endoscope, a fluid source adapted for connection to a needle to form a bleb in which a mucosal tissue layer is separated from underlying muscularis propria, a resection apparatus capable of attaching to the distal end of the endoscope, wherein the resection apparatus is capable of forming an opening through the underlying muscularis propria within the bleb whereby one or more devices may be advanced into, e.g., the peritoneal cavity or the posterior mediastinum through the opening; and closure materials capable of connecting the mucosal tissue layer to the underlying muscularis propria within the bleb, whereby the mucosal tissue layer covers the opening formed in the underlying muscularis propria.

As discussed herein, the methods of the present invention and the kits adapted for use in performing the methods include the components needed to form a bleb. Although as described herein the blebs may preferably be created using pressurized gas, it should be understood that the blebs could be formed by other fluids (e.g., liquids such as saline, etc.).

Figure 1:
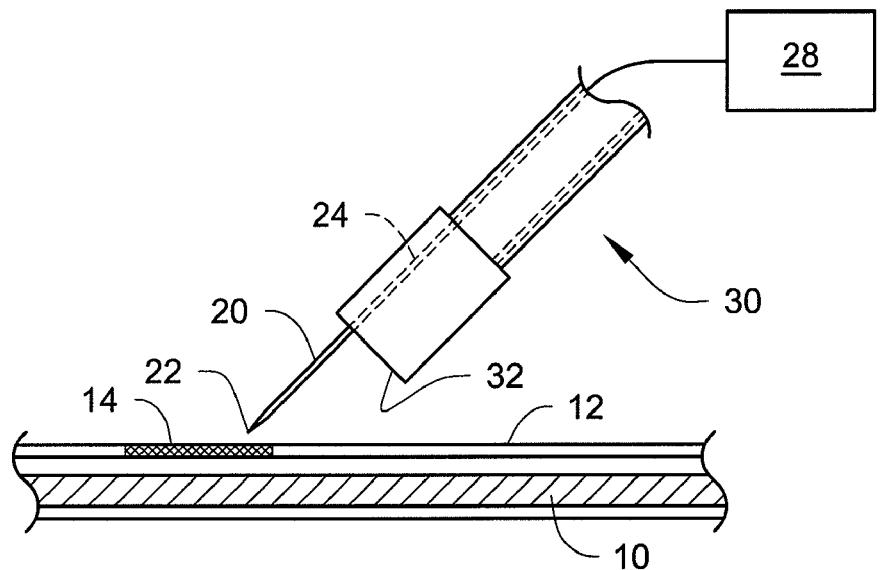
FIG. 1 is a cross-sectional view depicting initiation of submucosal fluid cushion formation in accordance with the present invention.

One exemplary apparatus for forming blebs useful in connection with the present invention is depicted in FIG. 1. The apparatus includes an elongated body 30 that has a distal end 32. The elongated body 30 may preferably be an endoscope with a suitable number of channels or lumens formed therein to accommodate the apparatus of the present invention.

The apparatus is depicted as positioned proximate a selected site 14 in tissue that includes mucosa 12 and underlying muscularis propria 10. The selected site 14 may preferably be found in the esophagus, stomach, etc. If the site 14 is in the esophagus, it may preferably be in the distal esophagus. It may be preferred, for example, that a bleb formed in the esophagus be positioned with an upper (proximal) end located 30 centimeters (cm) or less from the E-G junction, more preferably 15 cm or less from the E-G junction. In another manner of characterizing the position of the bleb, it may be preferred that the bleb be located between fourth and twelfth thoracic vertebra.

The depicted elongated body 30 includes a fluid delivery lumen 24 that extends through at least a portion of the elongated body 30. It may be preferred that the fluid delivery lumen 24 terminate proximate the distal end 32 of the elongated body 30. It may also be preferred that the fluid delivery lumen 24 extend proximally towards the proximal end (not shown) of the elongated body 30.

The apparatus depicted in FIG. 1 further includes a needle 20 that is preferably attached to the fluid delivery lumen 24 proximate the distal end 32 of the elongated body 30. The needle 20 may preferably be movable between an injection position in which the distal end 22 of the needle 20 extends from the distal end 32 of the elongated body 30 as seen in FIG. 1. It may also be preferred that the needle 20 be movable to a sheathed position in which the distal end 22 of the needle 20 does not extend past the distal end 32 of the elongated body 30, e.g., is retracted within the elongated body 30.

As an alternative to the depicted arrangement in which the fluid delivery lumen 24 is an integral part of the elongated body 30 with the needle 20 attached thereto, the needle may be attached to a separate body with its own fluid delivery lumen (in the form of, e.g., a catheter, tube, etc.) that can be advanced to the point at which the bleb is to be formed. Such a separate body and needle may be advanced through a lumen in the body 30 or it may be advanced outside of the body 30.

Figure 2:
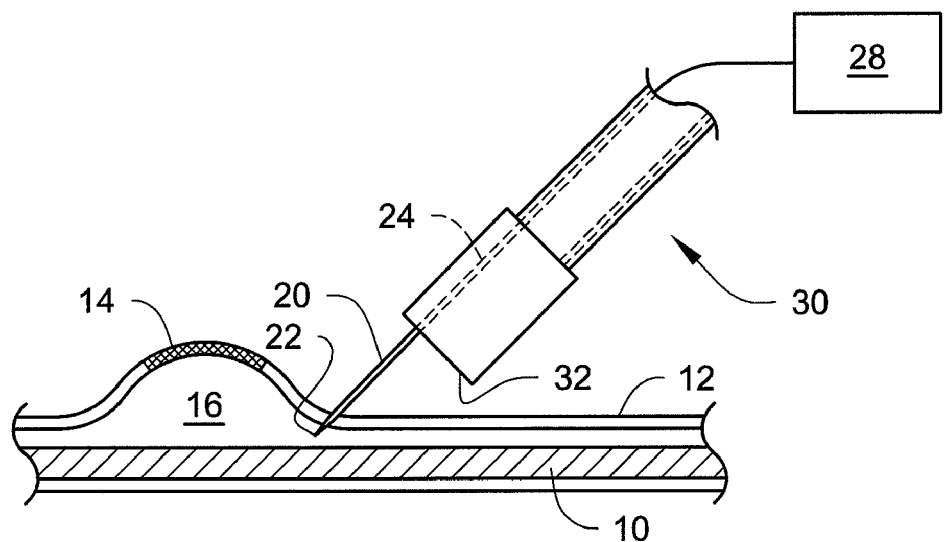
FIG. 2 is a partial cross-sectional view depicting formation of a submucosal fluid cushion in accordance with the present invention.

FIG. 2 depicts the apparatus of FIG. 1 after insertion of the distal end 22 of the needle 20 into the tissue proximate the selected site 14. It may be preferred that the needle 20 deliver a fluid into the tissue such that the mucosal tissue layer 12 is separated from the underlying muscularis propria 10 by a submucosal fluid cushion or bleb 16. The fluid used to form the submucosal fluid cushion 16 is preferably delivered through the needle 20, which is preferably in fluid communication with a fluid source 28 through the fluid lumen 24 extending through the elongated body 30.

The fluid source 28 may take a variety of forms depending on the fluids being supplied. The fluid source 28 may be pressurized such that the fluid can be dispensed through a valve (and preferably pressure regulator) without the need for a separate pump. In other instances, a pumping mechanism may be provided in combination with a reservoir that may or may not be pressurized. The pressure at which the fluid is delivered may vary, although it may be preferred that the pressure for gases be 20 psig (140 kPa) or more. Pressure control may be provided by, e.g., a regulator or other pressure control device.

The fluid used to form the submucosal fluid cushion 16 may be liquid, gas, or combination thereof. In some instances, it may be preferred that the fluid used to form the submucosal fluid cushion 16 be a liquid, e.g., saline solutions, sodium hyaluronate, glycerol solutions, methylcellulose solutions (such as those described in, e.g., U.S. Patent Application Publication No. 2003/0225460, titled COMPOSITIONS FOR GENERATING SUBMUCOSAL FLUID CUSHIONS, published Dec. 4, 2003), etc.

In other instances it may be preferred that the fluid used to from the submucosal fluid cushion 16 be a gas, e.g., a gas including gaseous carbon dioxide. In other instances, it may be preferred that the fluid consist essentially of one or more gases, e.g., consist essentially of gaseous carbon dioxide. Using a gaseous fluid to form submucosal fluid cushions may have advantages over submucosal fluid cushions formed using liquid fluids as discussed herein.

In some methods, it may be preferred to begin formation of the bleb with a small amount of saline to visually determine proper placement of the needle within the esophageal wall. Upon confirmation that the needle is properly positioned, pressurized gas can be used to enlarge the bleb and form gas-filled submucosal fluid cushion. In some methods, a sealant such as, e.g., 5% hydroxypropyl methylcellulose, may be injected into the gas-filled space of a bleb formed using gas to, e.g., limit gas escape from the bleb.

Figure 3:
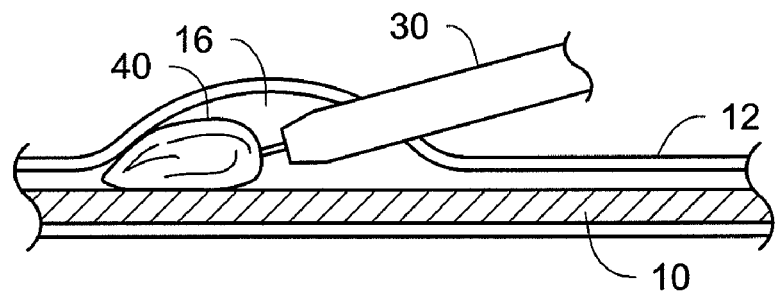
FIG. 3 is a partial cross-sectional view depicting advancement of a mechanical expansion device into the bleb.

With a gas-filled bleb formed which separates the mucosal tissue layer 12 from the underlying muscularis propria 10, it may be preferred that the bleb, or the area within which the mucosal tissue layer 12 is separated from the muscularis propria 10 may be expanded using a mechanical expansion device such as an inflatable balloon, cage, etc. The mechanical expansion device may preferably be advanced into the interior of the bleb (between the separated mucosal tissue layer 12 and the muscularis propria 10) through an opening formed in the mucosal tissue layer 12. FIG. 3 depicts advancement of the mechanical expansion device 40 into the bleb.

Once in position between the separated mucosal tissue layer 12 and the muscularis propria 10, the mechanical expansion device 40 may be expanded from a collapsed configuration in which the mechanical expansion device 40 is delivered into the bleb (by, e.g., passing through a lumen in the endoscope) and an expanded configuration in which the mechanical expansion device 40 expands to separate additional portions of the mucosal tissue layer 12 from the underlying muscularis propria 10 (if delivered through an endoscope lumen, the expanded configuration of the device 40 may preferably be larger than the lumen). The device 40 may be alternately expanded and collapsed as it is advanced to enlarge the amount of mucosal tissue layer 12 separated from the muscularis propria 10.

It may be preferred, for example, that the bleb (i.e., the area within which the submucosal tissue layer 12 is separated from the underlying muscularis propria 10) be expanded using a mechanical expansion device to have a length (measured along the length of the esophagus) of about 10 cm. The overall width (as measured around the circumference of the esophagus) may preferably remain relatively constant along the length of the bleb. Use of the mechanical expansion device 40 may be advantageous by providing some control over the direction(s) in which the bleb is enlarged after its initial formation.

Figure 4:
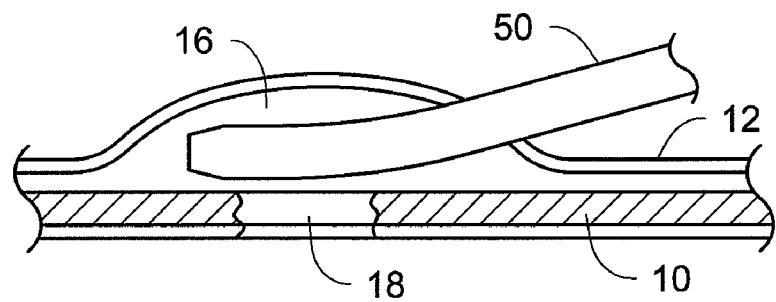
FIG. 4 is a partial cross-sectional view depicting an opening formed through the muscularis propria.

With the bleb enlarged to a desired size, the mechanical expansion device 40 may preferably be withdrawn from the bleb to allow for formation of an opening through the muscularis propria 10 within the bleb (i.e., within the area in which the mucosal tissue layer 12 is separated from the muscularis propria 10). Referring to FIG. 4, the opening 18 through the muscularis propria 10 may preferably be performed by resection using a cap-fitted endoscopic mucosal resection device 50 inserted into the bleb. It may be preferred that the resection be performed by drawing an ensnared portion of the muscularis propria 10 into the cap before performing the resection (using, e.g., electrosurgical current). Doing so may reduce or eliminate the risk of inadvertent surrounding organ injury by contact with the electrosurgical device performing the resection.

With the opening 18 formed in the muscularis propria 10, the resection apparatus may preferably be removed from the bleb to provide additional space for advancement of one or more devices into the bleb and through the opening 18 into, e.g., the peritoneal cavity, the mediastinum, etc. Such additional devices may include any device that is adapted for endoscopic delivery to an internal body location such as, for example, imaging devices, resection devices, etc. Care may be exercised so as not to injure the organs exposed within the peritoneal cavity, the mediastinum, etc.

In some instances, the transesophageal submucosal endoscopies performed using the methods and kits of the present invention may be performed with unmeasured air insufflation during unassisted voluntary ventilation. It may be preferred that transesophageal endoscopies according to the present invention be performed using an opening located in the distal esophagus and, further, that mechanical positive pressure ventilation be provided to reduce the likelihood or prevent acute lung decompression by any positive intramediastinal pressure. Monitoring air insufflation similar to pneumoperitoneum, as well as using carbon dioxide for insufflation, may improve the safety of the procedure.

Use of the methods and kits of the present invention may allow myotomy for the treatment of achalasia and also allow widespread mucosal resection to, e.g., undermine the mucosa for controlled en bloc excision. The submucosal endoscopic methods and kits of the present invention may also allow access to the cardiovascular and the peripheral respiratory systems.

When the access through the opening formed as a part of the submucosal endoscopy is no longer required, closure of the opening 18 in the muscularis propria 10 may preferably be accomplished by attaching the overlying mucosal tissue layer 12 to the muscularis propria 10 and or the surrounding mucosal tissue. In some instances, it may be sufficient to attach the mucosal tissue layer 12 to itself to close the opening through which the endoscope and other devices enter the bleb.

The kit of the present invention may preferably include tissue attachment materials to close the opening into the bleb and/or attach of the detached mucosal tissue layer 12 to the muscularis propria 10 and/or the mucosal tissue surrounding the bleb. The separated mucosal tissue layer 12 forms, in essence, a flap over the opening 18 in the muscularis propria 10 that, when reattached, seals or closes the opening 18 to reduce or prevent soiling of the mediastinum through the opening 18.

The tissue attachment materials may take a variety of forms such as, e.g., tissue anchors, tissue clips, adhesives, suture material, combinations of two or more elements, etc. For example, the tissue attachment materials included in a kit according to the present invention may include both tissue adhesives and tissue anchors.

Figure 5:
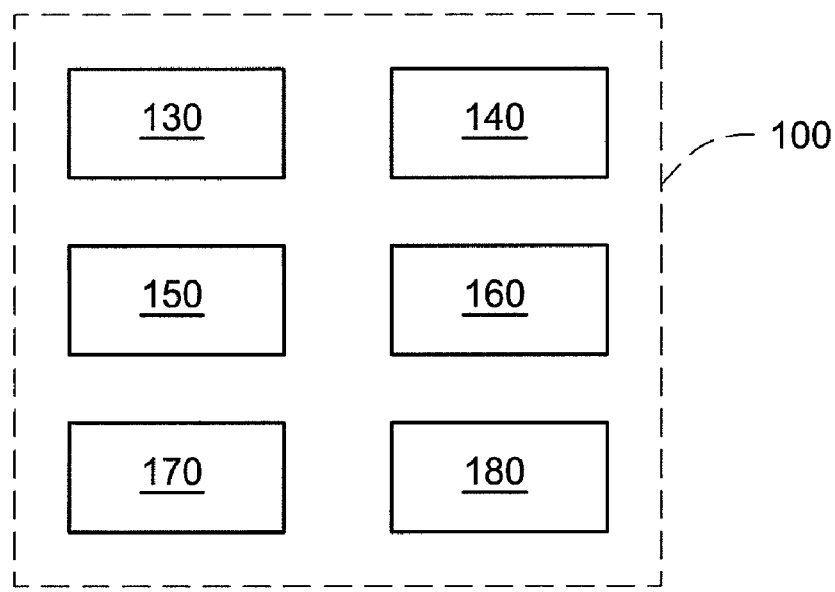
FIG. 5 is a schematic diagram of one exemplary embodiment of a kit according to the present invention.

As discussed herein, in addition to the methods of providing transesophageal access to the mediastinum, the present invention may also include kits with components selected to assist in performance of the methods. One such kit 100 is schematically depicted in FIG. 5 and may include an endoscope 130, a needle 140 with an associated fluid delivery lumen, a fluid source 150 adapted for connection to the fluid delivery lumen, a resection apparatus 160 capable of forming an opening through the underlying muscularis propria within a bleb, and closure materials 170 capable of connecting the separated mucosal tissue layer to cover an opening formed in the underlying muscularis propria within the bleb. Also depicted as a portion of the kit 100 is an optional mechanical expansion device 180 adapted for delivery into the bleb to expand a bleb initially formed using fluid pressure.

Examples of some potentially suitable devices that may be used in connection with the methods and kits of the present invention may include, e.g., a dual channel endoscope (e.g., a GIF 2T100B endoscope, Olympus America, Inc., Millville, N.Y.) with an endoscopic mucosal resection cap (EMR) (e.g., a 19 mm large EMR cap). The bleb may be formed by injecting gas through an injection needle, e.g., a standard 23 gauge injection needle (e.g., an Injector Force needle, Olympus America, Inc., Millville, N.Y.). Incisions may be made in the separated submucosal tissue layer to access the interior of the bleb using, e.g., a bipolar needle knife (e.g., a B-Knife, Zeon Medical Inc., Tokyo, Japan). Mechanical expansion of the blebs as discussed herein may be performed using, e.g., an inflatable balloon (e.g., a 15 mm biliary retrieval balloon such as a MULTI-3 balloon, Olympus America, Inc., Millville, N.Y.).

Examples of some potentially suitable tissue attachment materials that may be used in connection with the present invention may include, e.g., tissue clips (e.g., HX-6UR-1, Olympus America, Inc., Millville, N.Y.). Another option may include, e.g., tissue anchors (e.g., T-clip anchors from Olympus Japan, Tokyo, Japan). In place of or in addition to mechanical tissue attachments such as clips and anchors, the kits and methods of the present invention may include tissue adhesive (e.g., medical acrylate adhesive Indermil, Tyco Healthcare, Norwalk, Conn.).

Further details regarding other optional devices, apparatus, kits, and/or methods that may be useful in connection with the present invention may be described in U.S. patent application Ser. No. 11/920,220, filed Nov. 9, 2007, and titled APPARATUS AND METHODS FOR INTERNAL SURGICAL PROCEDURES (which is a National Stage application of PCT/US2006/018322, filed May 11, 2006, and published as International Application No. WO 2006/122279 on Nov. 16, 2006).

As used herein and in the appended claims, the singular forms "a," "and," and "the" include plural referents unless explicitly limited to the singular form or the context clearly dictates otherwise.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method for accessing the peritoneal cavity through the stomach, the method comprising:

delivering a fluid into mucosal tissue at a selected site in the stomach of a subject through a distal end of a fluid delivery lumen, wherein the fluid is delivered at a fluid pressure greater than the ambient atmospheric pressure, wherein the fluid separates the mucosal tissue to create a bleb in which a mucosal tissue layer is separated from underlying muscularis propria;

advancing an endoscope into the bleb through the separated mucosal tissue layer;

forming an opening through the muscularis propria of the stomach within the bleb, whereby one or more devices may be advanced into the peritoneal cavity through the opening; and covering the opening through the muscularis propria by re-attaching at least a portion of the separated mucosal tissue layer to the muscularis propria.

2. A method according to claim 1, wherein forming the opening comprises using an endoscopic mucosal resection cap attached to the distal end of the endoscope.

3. A method according to claim 1, wherein re-attaching the separated mucosal layer comprises using one or more tissue anchors.

4. A method according to claim 1, wherein covering the opening comprises using one or more tissue clips.

5. A method according to claim 1, wherein re-attaching the separated mucosal layer comprises applying adhesive to at least a portion of the separated mucosal tissue layer.

6. A method according to claim 1, further comprising enlarging the bleb by expanding a mechanical expansion device within the bleb after forming the bleb using the fluid.

7. A method according to claim 6, wherein the mechanical expansion device comprises an inflatable balloon.

8. A method according to claim 1, wherein the fluid in the fluid source comprises a gas, and wherein the gas is held at a pressure of 20 psig (140 kPa) or more.

9. A method for accessing the mediastinum through the esophagus, the method comprising:
   delivering a fluid into mucosal tissue at a selected site in the esophagus of a subject through a distal end of a fluid delivery lumen, wherein the fluid is delivered at a fluid pressure greater than the ambient atmospheric pressure, wherein the fluid separates the mucosal tissue to create a bleb in which a mucosal tissue layer is separated from underlying muscularis propria;
   advancing an endoscope into the bleb through the separated mucosal tissue layer;
   forming an opening through the muscularis propria of the esophagus within the bleb, whereby one or more devices may be advanced into the mediastinum through the opening; and
   covering the opening through the muscularis propria by re-attaching at least a portion of the separated mucosal tissue layer to the muscularis propria.

10. A method according to claim 9, wherein forming the opening comprises using an endoscopic mucosal resection cap attached to the distal end of the endoscope.

11. A method according to claim 9, wherein re-attaching the separated mucosal layer comprises using one or more tissue anchors.

12. A method according to claim 9, wherein covering the opening comprises using one or more tissue clips.

13. A method according to claim 9, wherein re-attaching the separated mucosal layer comprises applying adhesive to at least a portion of the separated mucosal tissue layer.

14. A method according to claim 9, further comprising enlarging the bleb by expanding a mechanical expansion device within the bleb after forming the bleb using the fluid.

15. A method according to claim 9, wherein the mechanical expansion device comprises an inflatable balloon.

16. A method according to claim 9, wherein the fluid in the fluid source comprises a gas, and wherein the gas is held at a pressure of 20 psig (140 kPa) or more.

* * * * *